(12) United States Patent
Reich et al.

(10) Patent No.: US 7,492,167 B2
(45) Date of Patent: Feb. 17, 2009

(54) METHOD AND DEVICE FOR MONITORING AND CONTROLLING FLUID LOCOMOTION

(75) Inventors: Ziv Reich, Ganei Yohanan (IL); Dan Shahar, Savyon (IL); Ruti Kapon, Ramat Gan (IL)

(73) Assignee: Yeda Research and Development Co. Ltd., Rechovot (IL)

( * ) Notice: Subject to any disclaimer, the term of this patent is extended or adjusted under 35 U.S.C. 154(b) by 756 days.

(21) Appl. No.: 10/700,588

(22) Filed: Nov. 5, 2003

(65) Prior Publication Data
US 2005/0092606 A1     May 5, 2005

(51) Int. Cl.
*G01R 27/26*     (2006.01)
(52) U.S. Cl. .................. 324/663; 324/660; 324/661; 324/664; 324/686
(58) Field of Classification Search .................. 324/660, 324/661, 663, 664, 686
See application file for complete search history.

(56) References Cited

U.S. PATENT DOCUMENTS

| | | | | |
|---|---|---|---|---|
| 3,545,271 | A | * 12/1970 | Amir et al. | ............... 73/861.41 |
| 4,105,028 | A | * 8/1978 | Sadlier et al. | ............ 73/861.41 |
| 5,922,537 | A | 7/1999 | Ewart et al. | |
| 6,107,626 | A | * 8/2000 | Wang et al. | ................. 250/288 |
| 6,323,660 | B1 | 11/2001 | Kunc et al. | |
| 6,562,012 | B1 | * 5/2003 | Brown et al. | ............. 73/861.12 |
| 6,633,172 | B1 | 10/2003 | Doemens et al. | |
| 2002/0092363 | A1 | * 7/2002 | Jorgenson et al. | ........ 73/861.95 |
| 2002/0118005 | A1 | * 8/2002 | Reich et al. | ................ 324/71.4 |

OTHER PUBLICATIONS

Hamill et al. "Improved Patch-Clamp Techniques for High-Resolution Current Recording From Cells and Cell-Free Membrane Patches", Pflügers Arch., 391: 85-100, 1981.
Kapon et al. "Method to Sense Single-Particle Motion Using A Tapered-Gap Microcapacitor", Applied Physics Letters, 84(21):4277-4270, 2004.

* cited by examiner

*Primary Examiner*—Timothy J Dole (57) ABSTRACT

A device for monitoring dripping of a fluid from a fluid channel, the device comprises a capacitor, being formed on or integrated with the fluid channel, and electrical contacts, connecting the capacitor to a capacitance measuring device, the capacitor is designed and constructed so that a change in a capacitance thereof represents a formation of a drop near an edge of the fluid channel.

54 Claims, 5 Drawing Sheets

METHOD AND DEVICE FOR MONITORING AND CONTROLLING FLUID LOCOMOTION

FIELD AND BACKGROUND OF THE INVENTION

The present invention relates to a device for monitoring and/or controlling fluid locomotion, method of manufacturing same, and methods of monitoring and/or controlling locomotion of fluid using same. More particularly, the present invention relates to methods and devices for monitoring and/or controlling dripping of fluid through capillaries, micropipettes, microchannels and the like.

Much industrial and academic effort is presently directed at the development of integrated micro devices or systems combining electrical, mechanical and/or optical/electrooptical components, commonly known as Micro Electro Mechanical Systems (MEMS). MEMS are fabricated using integrated circuit batch processing techniques and can range in size from micrometers to millimeters. These systems can sense, control and actuate on the micro scale, and function individually or in arrays to generate effects on the macro scale. MEMS include numerous applications, such as airbag accelerometers, ink-jet heads, radio frequency micro-switches for wireless communications, micro-gyroscopes, digital micro-mirror displays, pico-satellites and the like.

Whenever mechanics can replace electronics, it provides superior functionality and is not subject to undesirable electronic noise. For example, the classical electronic components of fiber-optic networks are now being replaced with optical MEMS switches that enable the creation of arrays of miniature high capacity switches which can play a critical role in the development of large-scale optical switches in fiber-optic networks.

In the most general form, MEMS consist of mechanical microstructures, microsensors, microactuators and electronics integrated in the same environment (e.g., on a silicon chip). The microfabrication technology enables fabrication of large arrays of devices, which individually perform simple tasks but in combination can accomplish complicated functions. For example, MEMS for guidance, navigation, motion control and high resolution flow visualization can provide experimental evidence about small-scale phenomena and thus verify fundamental principles in the microcosm.

One type of MEMS is a microfluidic device. Microfluidic devices include components such as channels, reservoirs, mixers, pumps, valves, chambers, cavities, reaction chambers, heaters, fluidic interconnects, diffusers, nozzles, and other microfluidic components. These microfluidic components typically have dimensions between a few micrometers and a few hundreds of micrometers. The small dimensions of the components minimize the physical size, the power consumption, the response time and the waste of the entire system. Such systems may provide wearable miniature devices located either outside or inside the human body.

Applications for microfluidic devices include genetic, chemical, biochemical, pharmaceutical, biomedical, chromatography, integrated circuit cooling, ink-jet printing, medical, radiological and environmental applications. The medical applications include diagnostic and patient management such as implanted drug dispensing systems. The environmental applications include detecting hazardous materials or conditions such as air or water pollutants, chemical agents, biological organisms or radiological conditions. The genetic and biochemical applications include testing and/or analysis of DNA, and other macro or smaller molecules, or reactions between such molecules in microfluidic devices, in an approach known as "lab-on-chip."

Microfluidic devices presently occupy an increasingly significant position in chemical and biochemical sensing, molecular separations, drug delivery and other forefront technologies. In a manner similar to that for microelectronics, microfluidic technologies enable the fabrication of highly integrated devices applicable to high throughput, low volume, automatable chemical and biochemical analyses and syntheses. Common fluids used in microfluidic devices include whole blood samples, bacterial cell suspensions, protein or antibody or nucleic acid solutions and various buffers.

Microfluidic devices can be used to obtain a variety of measurements including molecular diffusion coefficients, fluid viscosity, pH, chemical binding coefficients and enzyme reaction kinetics. Other applications for microfluidic devices include capillary electrophoresis, isoelectric focusing, immunoassays, flow cytometry, sample injection of proteins for analysis via mass spectrometry, sample injection of air or water samples for analysis via flamespectrometry, polymerase chain reaction (PCR) amplification, DNA analysis, cell manipulation, cell separation, cell patterning and chemical gradient formation. Many of these applications have utility for basic research and clinical diagnostics.

The development of miniaturized devices for chemical analysis and for synthesis and fluid manipulation is motivated by the prospects of improved efficiency, reduced cost and enhanced accuracy. Efficient, reliable manufacturing processes are a critical requirement for the cost-effective, high-volume production of devices that are targeted at high-volume, high-throughput test markets. In this respect, microfluidic devices are related to separation of components of a complex mixture for the purpose of analyzing the components individually without interference.

One separation method, particularly useful when the partition coefficients of the components (compounds) are similar, is known as high performance liquid chromatography (HPLC). In this method, the sample is entrained in a mobile phase, continuously flowing from one end of a column to the other. The sample is allowed to interact with a stationary phase bed present in the column in the form of a matrix or beads. As the mobile phase passes through the column, the compounds of the sample equilibrate between the mobile and stationary phases. Depending on the nature of the mobile phase, stationary phase and the components to be partitioned, the interacting time with the stationary phase vary from one component to the other, so that different compounds spend different fractions of time in the column, before arriving to its opposite end. This allows the various compounds in the sample to be physically separated along the column. A detection device detects the components when they elute from the column and measures the time spent in the column. Based on this time and the characteristics of the pulse generated by the detection device, the components are identified. The different components may also be individually collected.

Recently, microfluidic chromatography tubes have been developed. It is appreciated that the integration of such tubes on the same chips together with an efficient dripping and flowing monitor and/or controller is of utmost importance.

In the area of life science, microfluidic devices are used for fabricating microchips, such as DNA chips, protein chips and total analysis systems (also known as lab-on-chip). For example, DNA chips are fabricated on a substrate for which probes with known identity are used to determine complementary binding, thus allowing massive parallel gene expression and gene discovery studies. An experiment with a single DNA microarray can provide researchers information on thousands of genes simultaneously. The use of a microfluidic device in the fabrication process of a microchip facilitates the production of small and high-density spots on the substrate. Since only a small amount of solution is needed to make one chip, the cost of chip production is substantially reduced. In addition, a microfluidic device can created spots in consistent quantities and with uniform configurations, so as to enable highly accurate comparisons between spots.

Droplet microfluidics refers to the set of technologies that are being developed for manipulating very small, substantially uniform, liquid drops, micro- to nano-liters in volume, which are supported on a solid surface, sandwiched between two solid plates or sucked into a solid channel. The manipulations include moving the droplets around, making them coalesce, and breaking them up. These technologies have a promising potential for developing commercially viable droplet-based microfluidic platforms for biotechnology and other applications. The reason is that in pharmaceutical and bioanalysis applications, enormous savings can be realized by reducing the required amounts of expensive reagents to micro- or eventually nano-liter volumes. Moreover, the smaller the length scale over which transport processes (convection, diffusion and reaction) take place, the faster the completion time of the process. As such, the drive toward high-throughput screening and diagnostics requires the concomitant development of associated microfluidic enabling technologies.

Droplet microfluidics may be employed in the area of biochemical and biophysical investigations of single cells. Knowledge of cell activity may also be gained by measuring and recording electrical potential changes occurring within a cell, which changes depend on the type of cells, age of the culture and external conditions such as temperature or chemical environment. Thus, precisely controlling the physical and chemical environment of a cell under study significantly enhances the value of the research. Intracellular and extracellular electrical measurements have application in research studies of nerve cell bodies and tissue culture cells such as smooth muscle, cardiac, and skeletal muscle cells.

There are several major different technologies to measure the electrical activity of cells. Known in the art are techniques which are commonly called "patch clamp recordings" [O. P. Hamill et al., Pfleugers Arch. 391, 85-100, 1981], which have developed into very versatile and precise methods. These techniques allow researchers to observe the functioning of a single ionic channel, while monitoring a neuron's electrical activity in the brain, or allow the monitoring of the change in cell membrane area during a process of secretion, etc. The patch clamp technique provides exquisite resolution for measuring ionic currents in cell membranes, using a glass micropipette having an opening end of the order of 0.1 micron. The micropipette is filled with saline solution and is pressed gently onto the cell membrane, forming a stable physical high resistance electrical seal (in the GigaOhm range) on the cell membrane, commonly termed the Giga-seal. When suction is applied to the micropipette the cell membrane breaks and the cytoplasm and pipette solution start to intermix. Once this mixing is completed, the ionic environment in the cell is similar to the saline filling solution of the micropipette. Ionic currents in the cell membrane are thus indirectly determined by measuring the electrical potential of the solution filling the micropipette.

Another device for measuring the electrical activity of cells is an extracellular electrode, which is a microelectrode being attached to the cell membrane from the extracellular side. The capacitive coupling between the micro-electrode and the cell membrane alter the electrode potential which is used to determine and measure action potentials. As the extracellular electrode is only attached to the cell membrane from the outside, the cell membrane remains intact, and, provided that the appropriate conditions (temperature, pH, etc.) are supplied to the cell culture via an appropriate microfluidic platform, the cells can survive for a prolonged period of time.

In the area of brain research, it is believed that with the advent in microfluidic technology, complicated tasks such as mimicking the signaling of neural synapses on a single chip will become possible, leading to a better understanding of the human brain and neural system. In a typical neural network experiment, a network is composed of about $10^6$ neurons and glial cells, which are grown directly on top of a multi-electrode-array. The multi-electrode-array is a dense arrangement of microelectrodes which are used for parallel recording of the electrical activity of cells in a tissue slice or of cells grown in culture. Neurons, which are loosely placed above a particular microelectrode of the MEA form capacitance coupling with that electrode, hence allowing monitoring and recording of both the electrical activity and the electrical stimulation of the neuron.

Furthermore, efforts are being made to develop dense recording/stimulating microelectrode array probes for building an in-vivo electronic interface to the brain, which can deliver drugs at the cellular level using microfluidic channels. Integrated on each probe is a complete closed-loop fluidic control system, including flow meters, microvalves, and micropumps.

The ability to sense, monitor and/or control locomotion, such as dripping, of fluid through or from a microchannel or a micropipette is one of the fundamental properties required for all the above applications. Unlike dripping faucets, which have been studied extensively, monitoring devices in the micro scale are rather complicated systems, which, despite their ubiquitous application, have received little experimental or theoretical attention. Whereas in dripping faucets drop formation can be monitored, e.g., by ultra-fast video microscopy, equivalent methods for microfluidic applications are presently not known.

There is thus a widely recognized need for, and it would be highly advantageous to have, a method and device for monitoring and controlling fluid locomotion and microfluidic based applications and utilities incorporating same.

SUMMARY OF THE INVENTION

According to one aspect of the present invention there is provided a device for monitoring dripping of a fluid from a fluid channel, the device comprising a capacitor, being formed on or integrated with the fluid channel, and electrical contacts, connecting the capacitor to a capacitance measuring device, the capacitor is designed and constructed so that a change in a capacitance thereof represents a formation of a drop near an edge of the fluid channel.

According to another aspect of the present invention there is provided a device for controlling fluid locomotion in a fluid channel, the device comprising: (a) a capacitor, being formed on or integrated with the fluid channel and having a variable cross-sectional area; and (b) electrical contacts, connecting the capacitor to a voltage source; the capacitor being operable to induce polarization on molecules of the fluid so as to generate dielectrophoretic forces thereon thereby to control fluid locomotion.

According to further features in preferred embodiments of the invention described below, the device further comprising the capacitance measuring device and electronic circuitry, communicating with the capacitance measuring device and operable to signal an automatic system to selectively collect drops.

According to yet another aspect of the present invention there is provided a device for monitoring fluid locomotion in a fluid channel, the device comprising: (a) a capacitor, being formed on or integrated with the fluid channel and having a variable cross-sectional area; and (b) electrical contacts, connecting the capacitor to a capacitance measuring device; the variable cross-sectional area is selected so that a change in a capacitance of the capacitor represents a location of the fluid in the fluid channel.

According to still another aspect of the present invention there is provided a method of manufacturing a device for monitoring dripping of a fluid, the method comprising: (a) positioning a capacitor on a fluid channel in a manner that a change in a capacitance of the capacitor represents a formation of a drop near an edge of the fluid channel; and (b) connecting the capacitor to a capacitance measuring device using electrical contacts.

According to an additional aspect of the present invention there is provided a method of manufacturing a device for controlling fluid locomotion, the method comprising: (a) positioning a capacitor having a variable cross-sectional area on a fluid channel, the capacitor being operable to induce polarization on molecules of the fluid so as to generate dielectrophoretic forces thereon thereby to control fluid locomotion; and (b) connecting the capacitor to a voltage source using electrical contacts.

According to yet an additional aspect of the present invention there is provided a method of monitoring dripping of a fluid from a fluid channel, the method comprising continuously measuring capacitance changes of a capacitor being formed on or integrated with the fluid channel, and using the capacitance changes to monitor a formation of a drop near an edge of the fluid channel.

According to still an additional aspect of the present invention there is provided a method of controlling fluid locomotion in a fluid channel, the method comprising, using a variable cross-sectional area capacitor, being formed on or integrated with the fluid channel, for creating a non-uniform electric field capable of inducing polarization on molecules of the fluid, so as to generate dielectrophoretic forces on the molecules, thereby to control fluid locomotion.

According to a further aspect of the present invention there is provided a method of monitoring fluid locomotion in a fluid channel, the method comprising continuously measuring capacitance changes of a variable cross-sectional area capacitor being formed on or integrated with the fluid channel, and using the capacitance changes to determine a location of the fluid in the fluid channel at any time, thereby to monitor fluid locomotion.

According to further features in preferred embodiments of the invention described below, the step of positioning the capacitor comprises: (i) providing a pullable tube having a profile; (ii) pulling the tube at a controlled rate so as to provide a capillary having a predetermined profile; and (iii) applying two conductive plates on opposite faces of the capillary.

According to still further features in the described preferred embodiments the step of positioning the capacitor comprises: (i) providing a capillary; (ii) applying two conductive plates on opposite faces of the capillary; and (iii) filling the capillary with an HPLC stationary phase.

According to still further features in the described preferred embodiments the step of applying is effected from a procedure selected from the group consisting of evaporation, lift-off shadow-evaporation, nano-manipulation and focused ion milling.

According to still further features in the described preferred embodiments the step of positioning the capacitor comprises: (i) etching a non conductive substrate so as to provide a microchannel having walls; and (ii) applying two conductive plates on opposite walls of the microchannel.

According to still further features in the described preferred embodiments the step of applying the two conductive plates comprises coating the opposite walls by a conductive material.

According to still further features in the described preferred embodiments the step of applying the two conductive plates is by ion implantation.

According to still further features in the described preferred embodiments the step of connecting the capacitor to the capacitance measuring device is effected by a procedure selected from the group consisting of patterning, evaporation and ion implantation.

According to still further features in the described preferred embodiments the patterning is effected by a procedure selected from the group consisting of photolithography and lift-off technique.

According to still further features in the described preferred embodiments the electrical contacts comprise bonding pads.

According to still further features in the described preferred embodiments the capacitance measuring device is configured and designed to allow measuring of capacitance at a resolution of less than about 10% of a total capacitance of the capacitor.

According to still further features in the described preferred embodiments the capacitor is positioned in proximity to an edge of the fluid channel.

According to still further features in the described preferred embodiments the capacitor is positioned in proximity to an edge of the fluid channel, so as to control a shape and/or size of a drop formed near the edge.

According to still further features in the described preferred embodiments the fluid has a dielectric constant different than an ambient dielectric constant.

According to still further features in the described preferred embodiments the fluid is selected from the group consisting of water, a body fluid, a bacterial cell suspension, a protein solution, an antibody solution, a nucleic acid solution and ink.

According to still further features in the described preferred embodiments the two conductive plates have constant transverse dimensions along the longitudinal axis.

According to still further features in the described preferred embodiments the two conductive plates have a variable transverse dimensions along the longitudinal axis.

According to still further features in the described preferred embodiments the fluid channel is a capillary.

According to still further features in the described preferred embodiments the two conductive plates engage opposite faces of the capillary.

According to still further features in the described preferred embodiments the capillary has a profile selected from the group consisting of a polygonal profile, a circular profile, an ellipsoidal profile and an irregular pattern profile.

According to still further features in the described preferred embodiments the fluid channel is an HPLC column.

According to still further features in the described preferred embodiments the two conductive plates engage opposite faces of the HPLC column.

According to still further features in the described preferred embodiments the fluid channel is a microchannel of a microfluidic device.

According to still further features in the described preferred embodiments the two conductive plates engage opposite walls of the microchannel.

According to still further features in the described preferred embodiments the microfluidic device is selected from the group consisting of a drop ejector, a droplet microswitch, an extracellular electrode, a multi electrode array, a lab-on-chip device and a drug delivery microdevice.

According to still further features in the described preferred embodiments a size of the capacitor is in a nanometer scale.

According to still further features in the described preferred embodiments a size of the capacitor is in a millimeter scale.

According to still further features in the described preferred embodiments a size of the capacitor is in a centimeter scale.

According to still further features in the described preferred embodiments the capacitance measuring device is selected from the group consisting of a capacitance meter and a capacitance bridge.

The present invention successfully addresses the shortcomings of the presently known configurations by providing a device and method for monitoring and/or controlling fluid locomotion, enjoying properties far exceeding prior art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a device for monitoring and/or controlling fluid locomotion, which can be used in many fluid-based applications. Specifically, the present invention can be used to monitor and/or control locomotion (e.g., dripping) of fluid through capillaries, micropipettes, microchannels and the like. The present invention is further of a method of manufacturing the device, and methods of monitoring and/or controlling locomotion of a fluid using the device.

The principles and operation of a device and method for monitoring and/or controlling fluid locomotion according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Capacitance is a physical observable, attributed to a conductor or a system of conductors, which observable may be electrostatically defined as the ratio between a change in the electric charge on the conductor and the potential drop resulting from that change. The capacitance, C, of a capacitor depends on its geometry and on dielectric materials, if present, which are adjacent to the conducting components of the capacitor. For example, in a parallel-plate capacitor, sufficiently far from the edges of the plates, the capacity is proportional to the area of the plates, A, and to the dielectric coefficient of the dielectric material, $\epsilon$, and is inversely proportional to the distance between the plates, d.

This proportion, however, is rather inaccurate near the edges of the plates, where contributions of electric field lines present outside the inter-plate volume become significant. Edge effects have always been treated as limitations which are needed to be overcome, e.g., using large area plates with very small separation therebetween.

While conceiving the present invention it has been hypothesized, and while reducing the present invention to practice it has been demonstrated, that these edge effects can be directly exploited for the purpose of monitoring formation of fluid drops near the edges of the capacitor.

Figure 1:
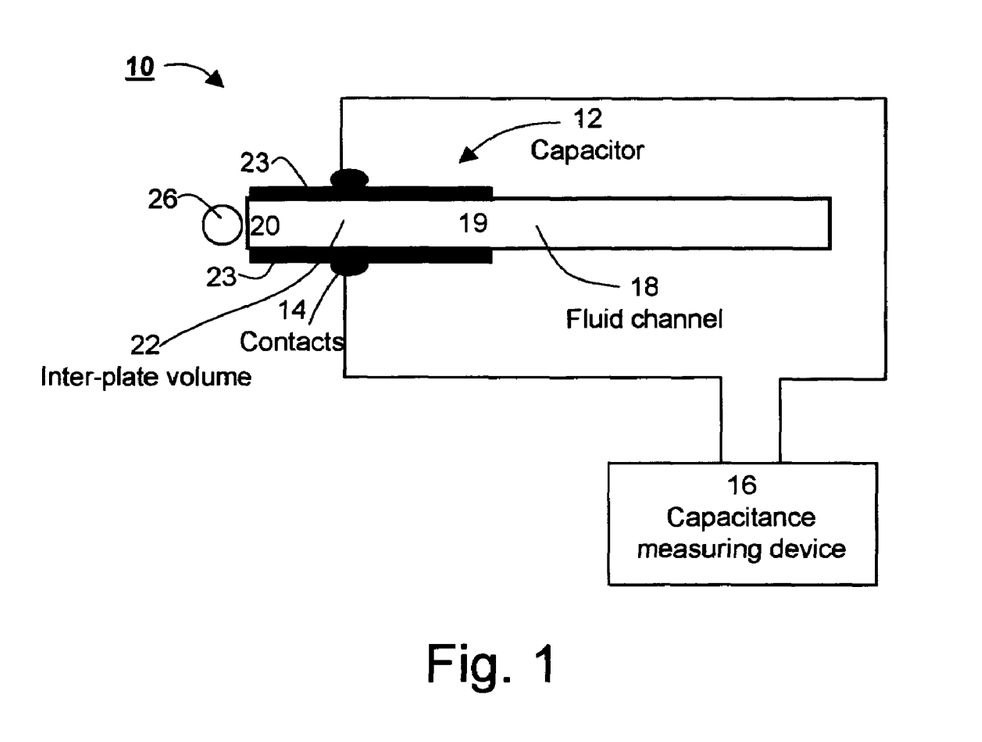
FIG. 1 is a schematic illustration of a device for monitoring dripping of a fluid from a fluid channel, according to a preferred embodiment of the present invention.

Hence, according to one aspect of the present invention there is provided a device for monitoring dripping of a fluid from a fluid channel, generally referred to herein as device 10. Device 10 is capable of monitoring dripping of any fluid having a dielectric constant which differs from the ambient (e.g., air) dielectric constant including, without limitation, water, a body fluid (e.g., blood, plasma, urine, saliva, vaginal secretions, feces and wound excrement), a bacterial cell suspension, a protein solution, an antibody solution, a nucleic acid solution, ink, different gases and the like.

Referring now to the drawings, FIG. 1 illustrates device 10 which, in its most basic form, comprises a capacitor 12, and electrical contacts 14 connecting capacitor 12 to a capacitance measuring device 16. Capacitor 12 typically comprises two plates 23 having edges 19 and 20, which may be either formed on, or integrated with, a fluid channel 18. Measuring device 16 serves for charging capacitor 12 and measuring the capacitance thereof.

Following is a description of the physical concepts of electric potential and electric field, which, for simplicity, is given for the case of a parallel-plate capacitor. It is to be understood that other types of capacitors are not excluded from the scope of the present invention.

The electric field, generated by the electrostatic charge of capacitor equals the gradient of the electric potential, which satisfies the Poisson equation. For any given boundary conditions, dictated by the geometry of the electrical system, the Poisson equation has a unique solution. For a parallel-plate capacitor, when the fluid is in a stationary state, the boundary conditions of the Poisson equation are such that, far from edges 19 and 20, the electric potential is substantially uniform in an inter-plate volume 22 defined by plates 23. Geometrically, the solution for the Poisson equation in inter-plate volume 22 is represented as a plurality of closed equipotential surfaces winding plates 23. Far from edges 19 and 20 the equipotential surfaces are substantially flat and parallel to plates 23, while near edges 19 and 20 the equipotential surfaces acquire a curvature.

Being the gradient of the electric potential, the electric field is perpendicular to the equipotential surfaces, hence directed from one plate (the positively charged plate) to the other (the negatively charged plate). Thus, the electric field lines are substantially straight in the center of inter-plate volume 22 and curved near edges 19 and 20.

When a fluid drop 26 is formed by the liquid in channel 18, say, near edge 20, the (curved) electric field near edge 20 induces a non-uniform polarization (e.g., charge distribution) on the surface of fluid drop 26. The polarization now serves as a secondary source, hence alters the boundary conditions of the Poisson equation and the corresponding electric potential. As stated, the electrostatic definition of a capacitance is the ratio between a change in the electric charge on the conductor and the potential drop resulting from that change. Thus, knowing the charge on capacitor 12, the measurement of its capacitance is practically an indirect measurement of the electric potential. As the electric potential depends on the shape and dielectric constant of fluid drop 26, one ordinarily skilled in the art would appreciate that a change in a capacitance of capacitor 12 represents a formation of drop 26 near edge 20.

A particular feature of the present invention is the real time measurement which, unlike prior art methods, allows a precise monitoring of the fluid drops from the beginning of their formation until they detached from channel 18, without the need for complicated post measurement analyses or large memory allocation for the data. Broadly speaking, the formation of fluid drop 26 typically increases the dielectric constant of the medium adjacent to edge 20 so that when fluid drop 26 starts to form, the capacitance of capacitor 12 increases, and when fluid drop 26 finally detaches from channel 18 there is a sudden decrement in the capacitance. In some rare cases, when the dielectric constant of the dripping fluid is smaller than the ambient dielectric constant, the behavior of the capacitance is reversed, i.e., in such cases, the formation of fluid drop 26 decreases the dielectric constant of the medium adjacent to edge 20 so that when fluid drop 26 starts to form, the capacitance of capacitor 12 decreases, and when fluid drop 26 detaches from channel 18 there is a sudden increase in the capacitance.

The formation stages of fluid drop 26 also depend on the properties of fluid channel 18. As further detailed hereinunder and demonstrated in the Examples section that follows, in one preferred embodiment of the present invention, fluid channel 18 is a capillary. In such small channels, fluids are subjected to several competing physical mechanisms, these are surface tension, capillarity and gravity.

The surface tension is explained as an enhancement of intermolecular interaction at the surface of the fluid. Cohesive forces between molecules present deep in the fluid are shared with all neighboring atoms. The surface molecules, on the other hand, have no neighboring atoms of the same type outside the fluid and exhibit stronger cohesive forces upon the molecules directly associated with them on the surface. The cohesive forces between like molecules compete with external forces existing between the molecules of the fluid and molecules of the surface. The surface tension increases as the ratio between the surface area and the volume of drop 26 increases. Thus, the first stage of the formation of drop 26 is dominated by the surface tension of the fluid. In this stage drop 26 has a spherical shape, the dielectric constant near edge 20 typically increases and the overall capacitance of capacitor 12 increases.

Capillary action is the result of a combination between the surface tension and external adhesion forces between molecules of the fluid and molecules of the walls of channel 18. The external adhesion force is a longitudinal force (parallel to the wall) which acts on the fluid at the contact region between the fluid and the wall and results in a formation of a meniscus on the fluid surface. The surface tension acts to hold the surface intact, so instead of just the edges moving in the direction of the force, the whole fluid surface is dragged backward into the channel.

The force of gravity is proportional to the mass of fluid drop 26, and as such becomes dominant only when the mass of fluid drop 26 becomes significant, i.e., when drop 26 contains a sufficient amount of fluid. As the drop becomes larger the gravitational force becomes larger and competes with the capillarity, so that drop 26 is pulled downward by the gravitational force and upward by the capillary action. This competition shapes drop 26 as an hourglass with a narrow neck. Typically, the capacitance during this stage starts to decrease because the volume of fluid in the immediate vicinity of edge 20 (hence also the dielectric constant) decreases. When the gravitational force is larger than the force accompanying the capillary action, the neck pinches off causing drop 26 to separate from the fluid column which remains behind in channel 18. Typically, at this stage, the capacitance of capacitor 12 experiences a sudden decrease.

According to a preferred embodiment of the present invention capacitor 12 is positioned in proximity to edge 20 of fluid channel 18, so as to better exploit the geometrical properties of the equipotential surfaces outside inter-plate volume 22, thereby to improve the sensitivity of device 10. Specifically, the distance between the edge of capacitor 12 and edge 20 is preferably less than about 10 nm, more preferably less than about 1 nm, most preferably about 0.1 nm.

As stated above, capacitor 12 is not limited to parallel-plate capacitors, and other shapes may be employed, provided that a change in the capacitance represents a formation of drop 26 near edge 20, as explained in detail hereinabove. For example capacitor 12 may comprise plates engaging opposite faces of a capillary having any profile, such as, but not limitedto, a polygonal profile, a circular profile an ellipsoidal profile and a profile having an irregular pattern.

According to a preferred embodiment of the present invention, capacitance measuring device 16 may be any know device capable of measuring or determining capacitance, such as, but not limited to, a capacitance meter and a capacitance bridge. Measuring device 16 detects a change in the capacitance of capacitor 12, which change, as stated herein represents the formation of drop 26. Hence, device 10 of the present invention, allows, following, for example, the generation of a simple calibration curve, to monitor the formation of drop 26 and its various stages of formation and detachment. A typical resolution of measuring device 16 is preferably less that about 10% (e.g., about 1%) of the total capacitance of 12. Better resolutions may be advantageous for some applications and can be achieved, if so required.

As used herein the term "about" refers to ±10%.

Device 10 is not limited by size. For example, one of ordinary skill in the art would appreciate that fluid channel 18 and capacitor 12 may be in nanometer to centimeter scale, inclusive, depending on the application to which device 10 is designed.

There are many applications in which dripping monitoring is important with which device 10 can be advantageously used as is further detailed and exemplified in the following.

For example, device 10 may be incorporated in an HPLC system, where the different components are individually collected into different containers (e.g., vials, tubes). As the physical separation on the HPLC column is achieved by generating different interaction times for different components (see the Background section or further detail), it is important to monitor the formation of drops at the tip of the HPLC column, which, at different times contain different components.

Hence, according to a preferred embodiment of the present invention fluid channel 18 is an HPLC column and capacitor 12 comprises two conductive plates engaging opposite faces of the HPLC column, preferably in close proximity to its tip. In this embodiment, device 10 can be used to count the number of drops eluted from the HPLC column, and to determine, based on this number, in which vial to collect the drop.

Being a real-time monitoring device which operates electronically, device 10 is optionally and preferably incorporated with an automatic system (e.g., a robot or a moving belt) which ensures that the correct vial is positioned under the HPLC column at any given time. In this embodiment, device 10 preferably comprises electronic circuitry, which, based on information received from device 16, signals the automatic system to select the appropriate container, by moving either the HPLC column or the container.

According to a preferred embodiment of the present invention fluid channel 18 may also be a microchannel of a microfluidic device, whereby plates 23 of capacitor 12 engage opposite walls of this microchannel. The microfluidic device is preferably a device in which the monitoring of drops formation is of interest. For example, in one embodiment, the microfluidic device is a drop ejector (e.g., an inkjet printing head or a device for preparing DNA microarrays), where the number and shape of the drops determine the quality of the final product.

In another embodiment the microfluidic device is a droplet microswitch, which takes advantage of the strong physical stability of droplets in micro scale. These devices employ fluid droplets which are maneuvered to a particular point in the device and are used for closing/opening electronic circuits. As these devices typically employ a conductive liquid (e.g., mercury), in this embodiment the plates of capacitor 12 are preferably coated by a thin layer for electrically isolating the conductive liquids from the plates.

In an additional embodiment, the microfluidic device is an extracellular electrode or a multi electrode array, which is used for measuring electrical activities in a cell culture and, at the same time, supplying nutrition thereto. In this embodiment device 10 is preferably used for real-time monitoring of the number of nutrition drops which are supplied to the cell culture.

As stated, the capacitor may have any size and shape. In particular the capacitor preferably has variable cross-sectional area, so that the equipotential surfaces are not parallel, and may also have a curvature, even far from the edges of the capacitor.

U.S. Patent Application No. 20020118005 to Reich et al., the contents of which are hereby incorporated by reference, discloses a device having a two-plate capacitor in which at least one of the parameters d, A or ϵ (respectively, the distance between the plates, the area of the plates and the dielectric coefficient of the dielectric material) is a function of a longitudinal axis of the capacitor. With such configuration, the capacitance of the capacitor becomes a function of a position along the longitudinal axis, so that when a conductive particle is present in the inter-plate volume, it induces a capacitance change which represents the position of the conductive particle along the longitudinal axis.

The capacitor of Reich et al. is successfully employed by the present invention. Unlike Reich et al., where the capacitor is used for the purpose of determining position or motion characteristics of conductive particles or molecules being attached to conductive particles, the present invention employs Reich's capacitor for the purpose of controlling and/or monitoring fluid locomotion (e.g., locomotion of a fluid drop) in a fluid channel.

Figure 2:
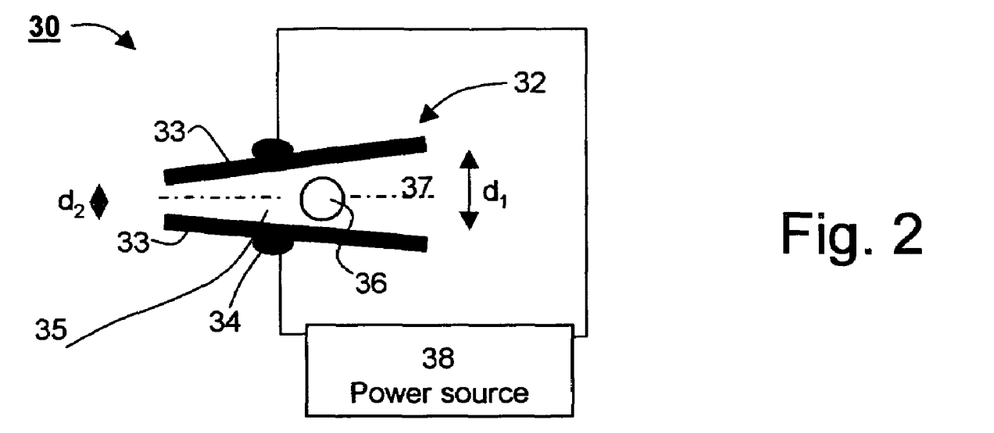
FIG. 2 is a schematic illustration of a device for controlling fluid locomotion in a fluid channel, according to a preferred embodiment of the present invention.

Hence, according to another aspect of the present invention there is provided a device 30 for controlling fluid locomotion in a fluid channel.

Reference is now made to FIG. 2, which is a schematic illustration of device 30. Device 30 comprises a capacitor 32, being formed on, or integrated with, a fluid channel (not shown in FIG. 2) and having a variable cross-sectional area, and electrical contacts 34, connecting capacitor 32 to a voltage source 38. The variable cross-sectional area of capacitor 32 ensures that, once capacitor 32 is charged, a non-uniform electrical filed is generated in inter-plate volume 35.

When an uncharged particle (which may be, for example, a fluid drop 36) is placed in a non-uniform electric field, it becomes polarized, i.e., acquires a non-zero electric dipole moment. The interaction between the electric dipole moment and the electric field results in net force acting on fluid drop 36, which force is proportional to the electric dipole moment and the gradient of the electric field, and is commonly termed a dielectrophoretic force.

Thus, when a voltage is applied by voltage source 38 on capacitor 32, dielectrophoretic forces generated by the non-uniform electric field maneuver drop 36 through the fluid channel. When drop 36 is formed near the edge, capacitor 32

(e.g., in a dripping device) the dielectrophoretic forces can be exploited to control the rate of drop formation as well as the shape of the drop. To facilitate such function, capacitor 32 is preferably positioned in proximity to the edge of the fluid channel (e.g., less than about 1 μm apart from the edge).

For example, when variable cross-sectional area capacitor 32 is incorporated with a droplet-based device (e.g., HPLC device, droplet ejector, extracellular electrode etc.), fluid drop 36 is subjected to the dielectrophoretic forces in addition to the above mentioned surface tension, capillarity and gravity. As the magnitude of the dielectrophoretic force is determined by the voltage supplied by voltage source 38, the rate of drop formation as well as its shape can be controlled by device 30. For example, to reduce the rate of drop formation the voltage on capacitor 32 can be selected so that the dielectrophoretic force successfully competes with the gravitational force, hence keeps drop 36 attached to the fluid column in the fluid channel for a longer period of time. The magnitude of the dielectrophoretic force may in addition or alternatively be selected so as to compete with the capillary action, for the purpose of preventing or delaying the formation of the above mentioned narrow neck.

Several configurations which enable a variable cross-sectional area capacitor are envisaged by the present invention. Such configurations are described in greater detail hereinbelow.

Hence, in one embodiment, specifically shown in FIG. 2, capacitor 32 is manufactured such that plates 33 have a variable distance between the paltes, hence defining inter-plate volume 55 of a variable-width. The variable distance is materialized by positioning plates 33 in a substantially non-parallel orientation, hence allowing the distance between the plates to vary from a maximal distance (denoted $d_1$ in FIG. 2) to a minimal distance (denoted $d_2$ in FIG. 2). Hence, capacitor 32 is characterized by a variable cross section at any position along its longitudinal axis 37. This embodiment is particularly relevant in fluid channels having a non parallel profile, e.g., capillaries and micropipettes.

Figure 3:
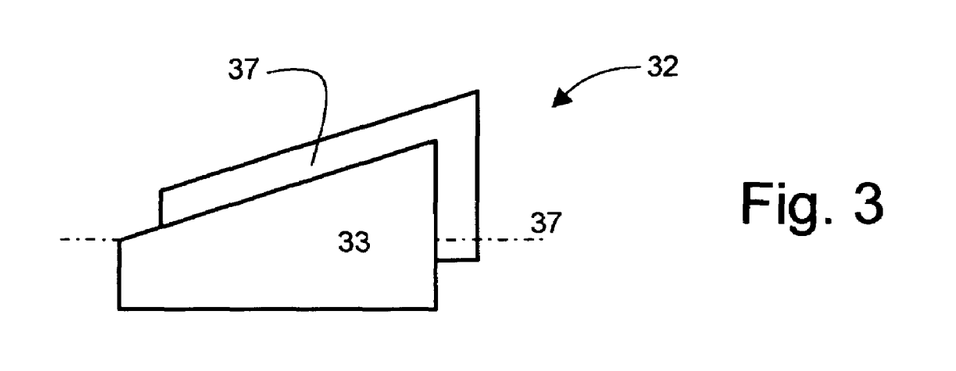
FIG. 3 is a schematic illustration of a two-plate capacitor in which a transverse dimension of the plates with respect to a longitudinal axis varies along the longitudinal axis, according to a preferred embodiment of the present invention.

In another embodiment, exemplified in FIG. 3, a transverse dimension of plates 33 with respect to longitudinal axis 37 varies along axis 37. For example, as is specifically shown in FIG. 3, plates 33 may have a trapezoidal shape, thereby providing a different effective area, A, at any position along longitudinal axis 37. In other words, at each point along axis 37, a unique cross-sectional area of inter-plate volume 35 is defined. This embodiment is particularly relevant in substrate-embedded fluid channels, such as, but not limited to, microchannels of microfluidic devices.

The locomotion of fluid drop 36 in the fluid channel causes changes in the capacitance of capacitor 32. This is due to the differences in the dielectric constants of the fluid and the medium present in inter-plate volume 35, air, as an example. The charge on plates 33 and the geometry of capacitor 32 are sufficient for calculating the unperturbed capacitance of capacitor 32, defined as the overall capacitance when no fluid is present in inter-plate volume 35. Any deviation from this unperturbed capacitance represents the presence of drop 36. The variable cross-sectional area of capacitor 32 makes its capacitance a function of the position of drop 36 along axis 37.

Thus, according to a preferred embodiment of the present invention, device 30 (or a similar device) is capable of monitoring locomotion of fluid through fluid channels, by measuring the capacitance of capacitor 32 (e.g., using capacitance measuring device 16, see FIG. 1) and determining, based on changes in the capacitance, the longitudinal position of drop 36.

Similarly to device 10 above, device 30 may be employed in numerous applications, for the purpose of controlling and/or monitoring fluid locomotion.

In one embodiment, device 30 is incorporated in a lab-on-chip device. A lab-on-chip device is typically a micro chemical-reactor or micro bio-reactor constructed on a substrate and designed to perform experiments or tests automatically. In this devices device 30 can be used for manipulate or dispense small volumes of fluid without the need of pumps or valves.

In another embodiment, device 30 is incorporated in a drug delivery microdevice. A drug delivery microdevice typically comprises a substrate having one or more microchannels, a plurality of hollow microneedles and a reservoir containing a drug, whereby the drug is to be transported from the reservoir through the substrate into the microneedles. Thus, device 30 may be formed on the walls of the microchannels so that the drug, under the influence of the dielectrophoretic forces generated by capacitor 32, is maneuvered through the microchannels device into the appropriate microneedle. Similar functions may be performed by device 30 in other microfluidic devices, such as, but not limited to, an extracellular electrode and a multi electrode array. Such drug may be, for example, a small compound or a protein, such as any hormone, e.g., growth factor or insulin in, for example, an aqueous or organic solution.

Additional examples of fluid-based applications in which device 30 may be employed, include, without limitations, the above mentioned HPLC system, drop ejector and droplet microswitch.

Other aspects of the present invention relate to methods of manufacturing devices 10 and 20, which are further described hereinunder.

Figure 4:
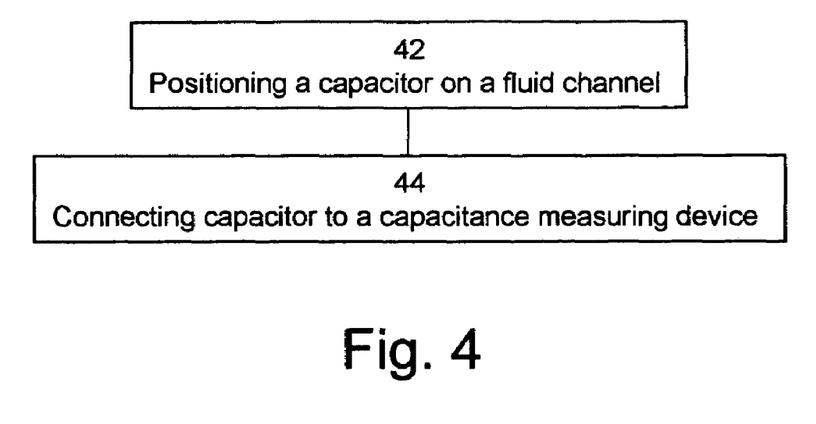
FIG. 4 is a flowchart of methods of manufacturing the devices of FIGS. 1-3, according to a preferred embodiment of the present invention.

Referring now again to the drawings, the methods generally comprise the following method steps which are illustrated in the flowchart of FIG. 4. Hence, in a first step, designated by Block 42, a capacitor (e.g., capacitor 12) is positioned (e.g., formed, applied) on the fluid channel, and a second step, designated by Block 44, the capacitor is connected to a capacitance measuring device. The capacitor is positioned in a manner that a change in a capacitance of capacitor represents a formation of a drop near an edge of fluid channel, as further detailed hereinabove.

According to a preferred embodiment of the present invention, the capacitor is formed on opposite faces of a capillary, a micropipette, an HPLC or any other tubular structure. This embodiment may be preceded by a step in which a pullable tube is pulled at a controlled rate so as to provide the capillary.

A suitable tube may be for example, a commercial 1 mm quartz pipette. The step of pulling the tube may be performed using any known technique conventionally employed for capillary generation, e.g., using a $CO_2$ laser based micropipette puller. The pulling conditions, i.e., laser intensity, and force of the pull tune the exact geometry of the formed capillary. For example, in a preferred embodiment in which a variable-width capacitor is employed (e.g., for the manufacturing of device 30), the pulling conditions are designed so as to produce tapered ends.

Once the capillary is provided, conductive plates are applied onto the capillary, so as to construct the capacitor. This may be done either onto opposite inner-faces or onto opposite outer-faces of the capillary. The plates may be applied using any technique know in the art such as evaporation, lift-off, shadow-evaporation, nano-manipulation and focused ion milling.

An alternative configuration contemplate by the present invention is a planar configuration of devices 10 or 30. Thus, according to a preferred embodiment of the present invention in the first step of the methods (Block 42, FIG. 4) opposite walls of a microfluidic device's microchannel are coated by a conductive material so as to provide the two plates of the capacitor. This step is preferably preceded by an optional step in which a nonconductive substrate is etched, so as to provide a microchannel.

Whether the microchannel is etched or otherwise formed or becomes available, and its walls are covered by the capacitor, the electrical contacts, are applied, e.g., by patterning and evaporation of a conductive material, onto the non conductive substrate. The electrical contacts serve for connecting the conductive plates of the capacitor to a capacitance measuring device and/or a voltage source, depending on the application to which devices 10 or 30 are designed.

According to a preferred embodiment of the present invention the nonconductive substrate employed is, for example, a poly-Si layer which is preferably deposited over a heavily doped Si wafer which, in addition to providing a base for the device, forms a ground plane shield. The patterning may comprise any constructive and/or destructive procedure known in the field of electronic microfabrication, for example, photolithography and lift-off techniques.

The conductive plates and the electrical contacts may be made of any electrically conductive material such as, but not limited to, gold, platinum, aluminum, copper, silver and the like. Alternatively, the conductive plates and/or the electrical contacts may be applied by selective implantation of ions into the poly-Si.

Figure 5:
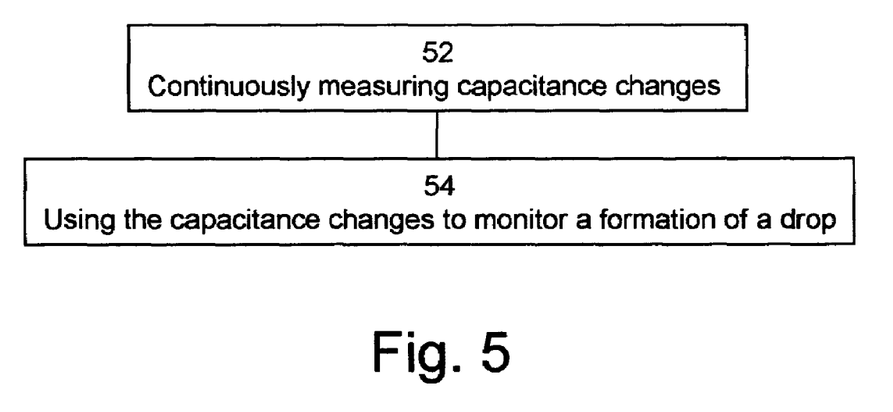
FIG. 5 is a flowchart of a method of monitoring dripping of a fluid from a fluid channel, according to a preferred embodiment of the present invention.

According to an additional aspect of the present invention there is provided a method of monitoring dripping of a fluid from a fluid channel. The method comprises the following method steps which are illustrated in the flowchart of FIG. 5. In a first step, designated by Block 52, capacitance changes of a capacitor formed on or integrated with the fluid channel are measured. In a second step, designated by Block 54, the capacitance changes are used for monitoring a formation of a drop near an edge of the fluid channel.

Figure 6:
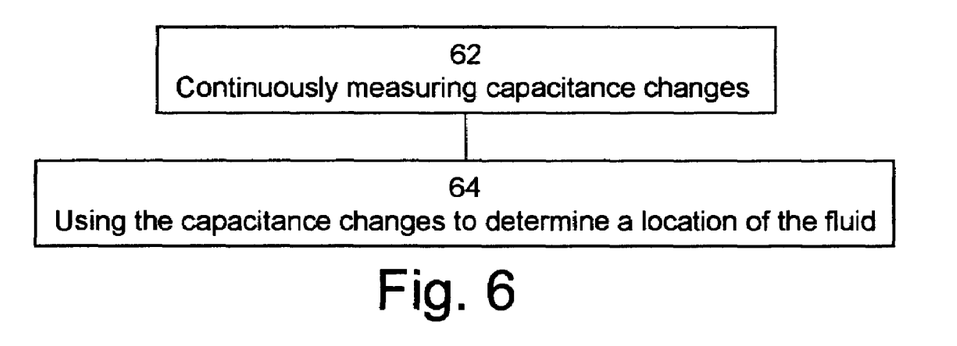
FIG. 6 is a flowchart of a method of monitoring fluid locomotion in a fluid channel, according to a preferred embodiment of the present invention.

According to still another aspect of the present invention there is provided a method of monitoring fluid locomotion in a fluid channel. The method comprises the following method steps which are illustrated in the flowchart of FIG. 6. In a first step, designated by Block 62, capacitance changes of a variable cross-sectional area capacitor, formed on or integrated with the fluid channel, are continuously measured. In a second step, designated by Block 64, the capacitance changes are used for determining a location of the fluid in the fluid channel at any time.

According to yet another aspect of the present invention there is provided a method of controlling fluid locomotion in a fluid channel. The method comprises the step of creating a non-uniform electric field using a variable cross-sectional area capacitor, formed on or integrated with the fluid channel. The non-uniform electric field is capable of inducing polarization in molecules of the fluid, so as to generate dielectrophoretic forces on molecules, thereby to control fluid locomotion.

It is expected that during the life of this patent many relevant fluid-based microelectronic systems will be developed and the scope of the term microfluidic device is intended to include all such new technologies a priori.

Additional objects, advantages and novel features of the present invention will become apparent to one ordinarily skilled in the art upon examination of the following example, which is not intended to be limiting. Additionally, each of the various embodiments and aspects of the present invention as delineated hereinabove and as claimed in the claims section below finds experimental support in the following example.

EXAMPLE

Hence, reference is now made to the following example, describing a prototype device of the present invention, and which together with the above descriptions, illustrates the invention in a non limiting fashion.

A Prototype Device

Materials and Methods

A measuring capacitor was formed by evaporation of metal plates onto two sides of a 10 µm round quartz capillary.

Figure 7:
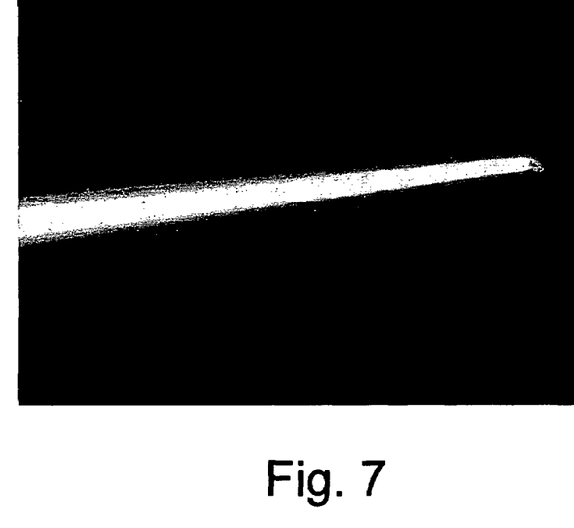
FIG. 7 is an image of a quartz capillary and two gold plates, according to a preferred embodiment of the present invention.

Reference is now made to FIG. 7 which is an image of the quartz capillary and the plates. The shape of the capillary dictated a non-parallel plate capacitor. The plates were fabricated by evaporation of a 50 Å layer of Ti or Cr, wetting the surface of the quartz and promoting adhesion of a 500 Å layer of gold which was subsequently evaporated thereon. The gold plates were extended several mm along the capillary to thereby serve as two connecting electrodes.

A syringe needle was glued to the upper end of the capillary to allow connection to a standard liquid handling system. The capillary was placed in a holder, specifically designed for the present experiment. The holder was positioned using a micromanipulator. The holder provides the electrical connection between the electrodes of the capillary and a capacitance measuring device.

The capillary was filled with deionized water and the capacitance was recorded by connecting the capacitor to one of the arms of a ratio-transformer capacitance bridge in a three-terminal scheme. A 5 V, 1 KHz probing voltage was than applied to the transformer, and the voltage on the balancing arm was measured using a lock-in detection scheme. When the bridge was fully balanced the lock-in showed a zero voltage drop across the balancing arm. As the water dripped from the capillary, the voltage on the balancing arm deviated due to the capacitance change. Thus the voltage on the balancing arm was proportional to the capacitance of the capillary. Signal acquisition was fully automated using GPIB™ communication protocols and Labview™ software (Purchased from National Instruments) and the signals were analyzed using Mathlab™ software.

Results and Discussion

Figure 8:
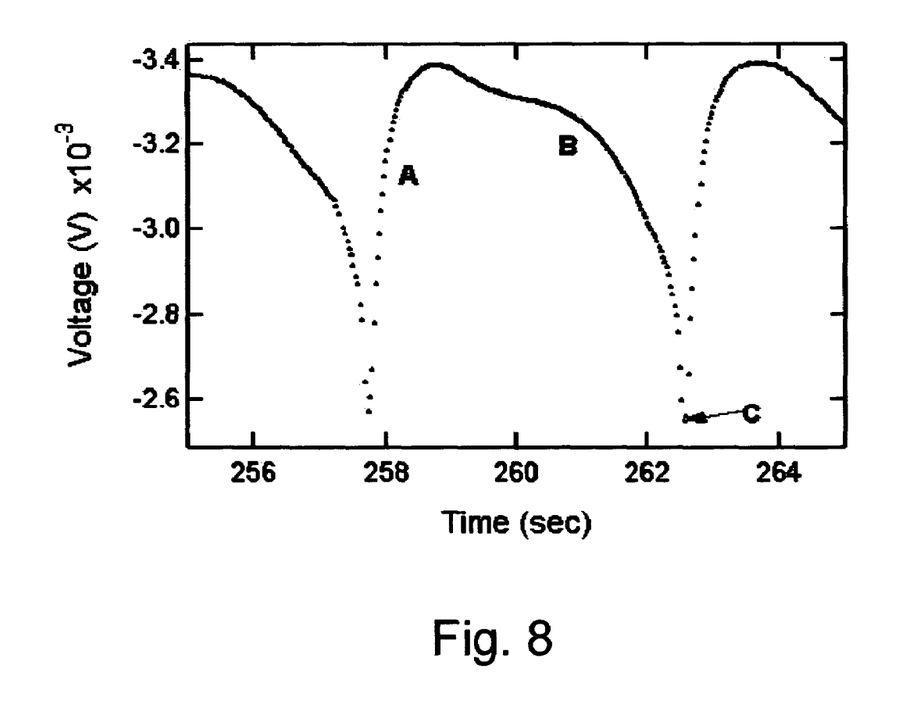
FIG. 8 shows a time trace of a voltage signal recorded from the quartz tube of FIG. 7, while water was dripping from its edge.

FIG. 8 shows the time trace of the voltage signal recorded from the quartz tube while water was dripping from its edge. The graph clearly shows a periodic signal corresponding to dripping from the capillary tube. This was verified by video recording. The average value of the capacitance is 1 pF and the changes are on the order of 0.01 pF.

The stages of the drop formation are designated on the graph of FIG. 8, as follows: the first stage, designated "A" on the graph, the surface tension is the main force and the liquid-air interface is substantially spherical. In the second stage, designated "B" on the graph, the drop becomes larger hence the role played by the gravitational force also increases. On the other hand, capillary action pulls the drop back into the tube, causing the drop to take the shape of an hourglass with a narrow neck. The capacitance during this stage decreases because the volume of liquid in the immediate vicinity of the capillary tip now decreases in time. In the third stage, designated "C" on the graph, the neck pinches off causing the drop to separate from the body of water in the capillary tube and the capacitance to drop sharply. This process repeats itself in an almost periodic way.

Figure 9:
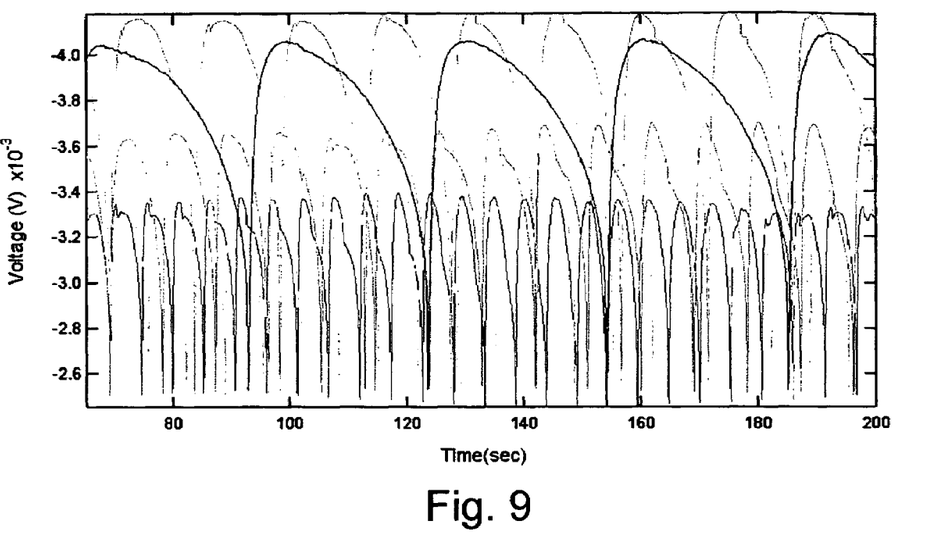
FIG. 9 shows the capacitance of the quartz tube of FIG. 7 for various drip rates.

FIG. 9 shows the capacitance recorded, in the manner just described, for various drip rates. Periodic patterns, representing successive formation and detaching of water drops, are clearly seen for all drip rates.

Figure 10:
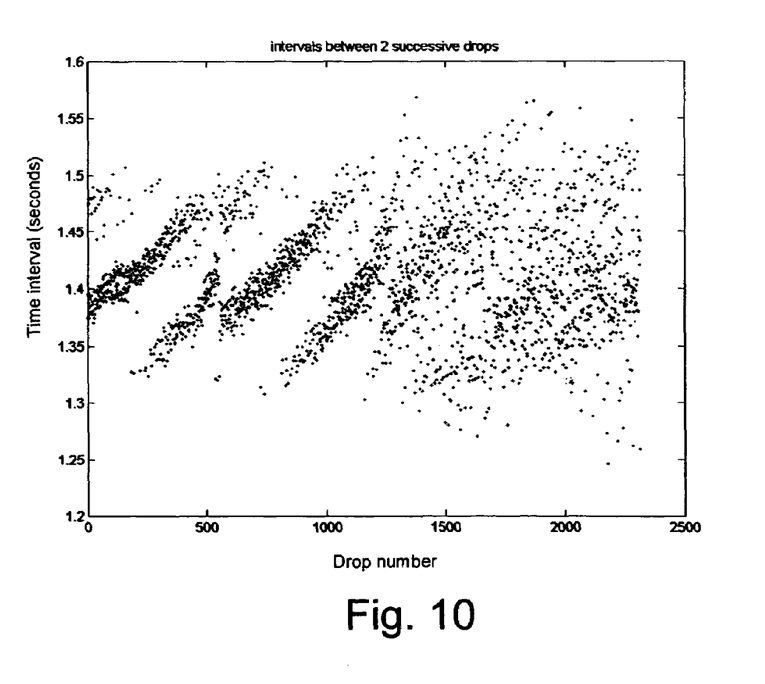
FIG. 10 shows the periodicity (time interval between successive drops) of a dripping-capillary as a function of drop number.

FIG. 10 shows the periodicity (time interval between successive drops) of a dripping-capillary as a function of drop number. The system clearly exhibits rich nonlinear dynamics.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for monitoring fluid locomotion in a fluid channel, the device comprising:
   (a) a capacitor, being formed on or integrated with the fluid channel and having a variable cross-sectional area; and
   (b) electrical contacts, connecting said capacitor to a capacitance measuring device;
   said variable cross-sectional area is selected so that a change in a capacitance of said capacitor represents a location of the fluid in the fluid channel wherein the fluid channel is an HPLC column.

2. The device of claim 1, wherein the fluid is selected from the group consisting of water, a body fluid, a bacterial cell suspension, a protein solution, an antibody solution, a nucleic acid solution and ink.

3. The device of claim 1, wherein said capacitor is positioned in proximity to an edge of the fluid channel, so as to monitor a rate of drop formation near said edge.

4. The device of claim 1, wherein said capacitor comprises two conductive plates defining an inter-plate volume having a longitudinal axis, said conductive plates having constant transverse dimensions along said longitudinal axis.

5. The device of claim 1, wherein said capacitor comprises two conductive plates defining an inter-plate volume having a longitudinal axis, said conductive plates having a variable transverse dimensions along said longitudinal axis.

6. The device of claim 1, wherein said capacitor comprises two conductive plates engaging opposite faces of said HPLC column.

7. The device of claim 1, wherein said capillary has a profile selected from the group consisting of a polygonal profile, a circular profile, an ellipsoidal profile and an irregular pattern profile.

8. The device of claim 1, wherein said capacitor comprises two conductive plates engaging opposite faces of said HPLC column.

9. The device of claim 1, wherein a size of said capacitor is in a nanometer scale.

10. The device of claim 1, wherein a size of said capacitor is in a millimeter scale.

11. The device of claim 1, wherein a size of said capacitor is in a centimeter scale.

12. The device of claim 1, wherein said capacitance measuring device is selected from the group consisting of a capacitance meter and a capacitance bridge.

13. The device of claim 1, wherein said capacitance measuring device is configured and designed to allow measuring of capacitance at a resolution of less than about 10% of a total capacitance of said capacitor.

14. A method of monitoring fluid locomotion in a fluid channel, the method comprising continuously measuring capacitance changes of a variable cross-sectional area capacitor being formed on or integrated with the fluid channel, the fluid channel being an HPLC column; and
   using said capacitance changes to determine a location of the fluid in the fluid channel at any time, thereby to monitor fluid locomotion.

15. The method of claim 14, wherein the fluid is selected from the group consisting of water, a body fluid, a bacterial cell suspension, a protein solution, an antibody solution, a nucleic acid solution and ink.

16. The method of claim 14, wherein said capacitor is positioned in proximity to an edge of the fluid channel, so as to monitor of a rate of drop formation near said edge.

17. The method of claim 14, wherein said capacitor comprises two conductive plates defining an inter-plate volume having a longitudinal axis, said conductive plates having constant transverse dimensions along said longitudinal axis.

18. The method of claim 14, wherein said capacitor comprises two conductive plates defining an inter-plate volume having a longitudinal axis, said conductive plates having a variable transverse dimensions along said longitudinal axis.

19. The method of claim 14, wherein said capacitor comprises two conductive plates engaging opposite faces of said capillary.

20. The method of claim 14, wherein said HPLC column has a profile selected from the group consisting of a polygonal profile, a circular profile, an ellipsoidal profile and an irregular pattern profile.

21. The method of claim 14, wherein said capacitor comprises two conductive plates engaging opposite faces of said HPLC column.

22. The method of claim 14, wherein a size of said capacitor is in a nanometer scale.

23. The method of claim 14, wherein a size of said capacitor is in a millimeter scale.

24. The method of claim 14, wherein a size of said capacitor is in a centimeter scale.

25. The method of claim 14, wherein said capacitance measuring device is selected from the group consisting of a capacitance meter and a capacitance bridge.

26. The method of claim 14, wherein said capacitance measuring device is configured and designed to allow measuring of capacitance at a resolution of less than about 10% of a total capacitance of said capacitor.

27. A device for monitoring fluid locomotion in a fluid channel, the device comprising:
   (a) a capacitor, being formed on or integrated with the fluid channel and having a variable cross-sectional area; and
   (b) electrical contacts, connecting said capacitor to a capacitance measuring device;
   said variable cross-sectional area is selected so that a change in a capacitance of said capacitor represents a location of the fluid in the fluid channel, wherein the fluid channel is a microchannel of a microfluidic device.

28. The device of claim 27, wherein the fluid is selected from the group consisting of water, a body fluid, a bacterial cell suspension, a protein solution, an antibody solution, a nucleic acid solution and ink.

29. The device of claim 27, wherein said capacitor is positioned in proximity to an edge of the fluid channel, so as to monitor a rate of drop formation near said edge.

30. The device of claim 27, wherein said capacitor comprises two conductive plates defining an inter-plate volume having a longitudinal axis, said conductive plates having constant transverse dimensions along said longitudinal axis.

31. The device of claim 27, wherein said capacitor comprises two conductive plates defining an inter-plate volume having a longitudinal axis, said conductive plates having a variable transverse dimensions along said longitudinal axis.

32. The device of claim 27, wherein said capacitor comprises two conductive plates engaging opposite faces of said microchannel.

33. The device of claim 27, wherein said microchannel has a profile selected from the group consisting of a polygonal profile, a circular profile, an ellipsoidal profile and an irregular pattern profile.

34. The device of claim 27, wherein said capacitor comprises two conductive plates engaging opposite walls of said microchannel.

35. The device of claim 27, wherein said microfluidic device is selected from the group consisting of a drop ejector, a droplet microswitch, an extracellular electrode, a multi electrode array, a lab-on-chip device and a drug delivery microdevice.

36. The device of claim 27, wherein a size of said capacitor is in a nanometer scale.

37. The device of claim 27, wherein a size of said capacitor is in a millimeter scale.

38. The device of claim 27, wherein a size of said capacitor is in a centimeter scale.

39. The device of claim 27, wherein said capacitance measuring device is selected from the group consisting of a capacitance meter and a capacitance bridge.

40. The device of claim 27, wherein said capacitance measuring device is configured and designed to allow measuring of capacitance at a resolution of less than about 10% of a total capacitance of said capacitor.

41. A method of monitoring fluid locomotion in a fluid channel, the method comprising:
continuously measuring capacitance changes of a variable cross-sectional area capacitor being formed on or integrated with the fluid channel, the fluid channel being a microchannel of a micro fluidic device, and
using said capacitance changes to determine a location of the fluid in the fluid channel at any time, thereby to monitor fluid locomotion.

42. The method of claim 41, wherein the fluid is selected from the group consisting of water, a body fluid, a bacterial cell suspension, a protein solution, an antibody solution, a nucleic acid solution and ink.

43. The method of claim 41, wherein said capacitor is positioned in proximity to an edge of the fluid channel, so as to monitor of a rate of drop formation near said edge.

44. The method of claim 41, wherein said capacitor comprises two conductive plates defining an inter-plate volume having a longitudinal axis, said conductive plates having constant transverse dimensions along said longitudinal axis.

45. The method of claim 41, wherein said capacitor comprises two conductive plates defining an inter-plate volume having a longitudinal axis, said conductive plates having a variable transverse dimensions along said longitudinal axis.

46. The method of claim 41, wherein said capacitor comprises two conductive plates engaging opposite faces of said microchannel.

47. The method of claim 41, wherein said microchannel has a profile selected from the group consisting of a polygonal profile, a circular profile, an ellipsoidal profile and an irregular pattern profile.

48. The method of claim 41, wherein said capacitor comprises two conductive plates engaging opposite walls of said microchannel.

49. The method of claim 41, wherein said microfluidic device is selected from the group consisting of a drop ejector, a droplet microswitch, an extracellular electrode, a multi electrode array, a lab-on-chip device and a drug delivery microdevice.

50. The method of claim 41, wherein a size of said capacitor is in a nanometer scale.

51. The method of claim 41, wherein a size of said capacitor is in a millimeter scale.

52. The method of claim 41, wherein a size of said capacitor is in a centimeter scale.

53. The method of claim 41, wherein said capacitance measuring device is selected from the group consisting of a capacitance meter and a capacitance bridge.

54. The method of claim 41, wherein said capacitance measuring device is configured and designed to allow measuring of capacitance at a resolution of less than about 10% of a total capacitance of said capacitor.

* * * * *